(12) United States Patent
Panin et al.

(10) Patent No.: US 11,874,411 B2
(45) Date of Patent: Jan. 16, 2024

(54) ESTIMATION OF PARTIALLY MISSING ATTENUATION IN TIME-OF-FLIGHT POSITRON EMISSION TOMOGRAPHY

(71) Applicant: Siemens Medical Solutions USA, Inc., Malvern, PA (US)

(72) Inventors: Vladimir Panin, Knoxville, TN (US); Deepak Bharkhada, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 719 days.

(21) Appl. No.: 16/948,554

(22) Filed: Sep. 23, 2020

(65) Prior Publication Data
US 2022/0091286 A1    Mar. 24, 2022

(51) Int. Cl.
| | | |
|---|---|---|
| *A61B 6/03* | (2006.01) | |
| *G06N 3/02* | (2006.01) | |
| *G06F 18/214* | (2023.01) | |
| *G01T 1/29* | (2006.01) | |
| *G01T 1/20* | (2006.01) | |
| *G06T 11/00* | (2006.01) | |

(52) U.S. Cl.
CPC ............ *G01T 1/2985* (2013.01); *A61B 6/032* (2013.01); *A61B 6/037* (2013.01); *G01T 1/2018* (2013.01); *G06F 18/214* (2023.01); *G06N 3/02* (2013.01); *G06T 11/008* (2013.01)

(58) Field of Classification Search
None
See application file for complete search history.

(56) References Cited

U.S. PATENT DOCUMENTS

| | | | |
|---|---|---|---|
| 9,155,514 B2 | 10/2015 | Panin | |
| 2015/0036789 A1* | 2/2015 | Panin | G06T 11/006 378/4 |
| 2019/0188884 A1* | 6/2019 | Zhu | G06T 7/11 |
| 2019/0266728 A1* | 8/2019 | Lee | A61B 6/037 |

(Continued)

OTHER PUBLICATIONS

Hwang, Donghwi, et al. "Generation of PET attenuation map for whole-body time-of-flight 18F-FDG PET/MRI using a deep neural network trained with simultaneously reconstructed activity and attenuation maps." Journal of Nuclear Medicine 60.8 (2019): 1183-1189.

(Continued)

*Primary Examiner* — Idowu O Osifade (57) ABSTRACT

Positron emission tomography (PET) with partially known attenuation accounts for the missing attenuation. Since a computed tomography (CT) scan may provide attenuation for less than all the locations used in PET reconstruction, artificial intelligence corrects for the missing attenuation. For example, the unknown attenuation or attenuation correction factors are estimated by the artificial intelligence. The known and estimated attenuations or correction factors are used in the PET reconstruction, providing more uniform PET sensitivity and better accounting for scatter. As another example, the artificial intelligence alters intensity of the activity in some locations to account for reconstruction with missing attenuation information, correcting for sensitivity variation and/or lack of scatter information for some locations.

20 Claims, 3 Drawing Sheets

(56) References Cited

U.S. PATENT DOCUMENTS

2022/0047227 A1* 2/2022 Heukensfeldt Jansen .................. A61B 6/5235

OTHER PUBLICATIONS

Leynes, Andrew P., et al. "Zero-echo-time and Dixon deep pseudo-CT (ZeDD CT): direct generation of pseudo-CT mages for pelvic PET/MRI attenuation correction using deep convolutional neural networks with multiparametric MRI." Journal of Nuclear Medicine 59.5 (2018): 852-858.

* cited by examiner

ESTIMATION OF PARTIALLY MISSING ATTENUATION IN TIME-OF-FLIGHT POSITRON EMISSION TOMOGRAPHY

BACKGROUND

The present embodiments relate to positron emission tomography (PET). In PET, attenuation information is used in reconstruction. The attenuation is derived from a computed tomography (CT) or another x-ray scan. There is a desire to limit the use of x-rays.

A three-dimensional PET scanner acquires oblique lines of response (LORs) in addition to the direct plane LORs. As a result, the edge axial planes of the reconstructed volume suffer from a lower sensitivity than the central axial planes because the edge axial planes are reconstructed from a smaller set of oblique LORs. A CT scan, which is acquired first, defines the axial extent of the reconstructed volume. Typically, the axial coverage length is chosen in such a way that a certain number of overlapping PET bed positions completely sample the reconstruction volume. The bed overlap is designed to achieve a uniform sensitivity by summing the roughly triangular axial sensitivity profiles corresponding to each bed position. Nevertheless, the edge planes of the last bed acquisition still have a lower sensitivity because only direct plane LORs are available. This problem can be solved by acquiring an additional bed position, so as to make the axial sensitivity more uniform throughout the CT defined volume. The problem is not yet solved however, because the attenuation correction factors (ACFs) for some oblique LORs are not available from the CT scan because these LORs are passing outside the CT defined volume. As a result, the edge axial planes would still suffer from a lower sensitivity if only LORs with CT-known ACFs are used during reconstruction. The missing attenuation information may also impact scatter estimation. Increasing x-ray dose to increase the CT volume is not desired.

To avoid this issue, reconstruction may be performed without x-ray-based attenuation information. In PET, simultaneous emission activity and attenuation map reconstruction in non-time-of-flight (TOF) PET has been a topic of investigation in order to exclude the x-ray transmission sources completely. Both distributions are assumed to be reconstructed from a single emission data set. A significant amount of information about attenuation is contained in the emission data. The artifact of cross-talking between the activity and the attenuation images, when the activity image features propagate to attenuation map images and vice versa, is difficult to avoid.

Theoretical investigations concluded that both activity and attenuation distributions may be determined from PET TOF data up to an activity image scaling parameter. These advances encouraged investigation of practical applications of transmission less TOF reconstruction. One limitation of this approach is that the attenuation information cannot be determined outside of the emission sinogram support. In addition, the solution may not be sufficiently stable. Therefore, the practical application might still require a priori knowledge of the attenuation. Recent examples of simultaneous activity and attenuation reconstruction in TOF PET indeed use a significant amount of prior information. MRI data may be used to define regions of uniform attenuation and estimate the attenuation coefficient in each region from the emission TOF data. Derived truncated attenuation map regions have been used in the application for PET-MRI. Another example is the use of additional external nuclear transmission sources. This approach is difficult when using emission data alone for general cases, such as when attenuation map support is larger compared to activity image support.

BRIEF SUMMARY

By way of introduction, the preferred embodiments described below include methods, systems, and non-transitory computer readable media for reconstruction in PET, such as TOF PET, with partially known attenuation. Since the CT scan may provide attenuation for less than all the locations used in PET reconstruction, artificial intelligence corrects for the missing attenuation. For example, the unknown attenuation or attenuation correction factors are estimated by the artificial intelligence. The known and estimated attenuations or correction factors are used in the PET reconstruction, providing more uniform PET sensitivity and better accounting for scatter. As another example, the artificial intelligence alters intensity of the activity in some locations to account for reconstruction with missing attenuation information, correcting for sensitivity variation and/or lack of scatter information for some locations.

In a first aspect, a method is provided for reconstructing in positron emission tomography with partially known attenuation. A computed tomography (CT) scanner acquires first attenuation information for a CT volume of a patient. The first attenuation is the partially known attenuation. A positron emission tomography (PET) scanner having a plurality of detectors acquires time-of-flight data along lines-of-response from emissions. The first attenuation information is available for a first subset of the lines-of-response and unavailable for at least parts of the lines of response of a second subset of the lines-of-response. A machine-trained neural network generates second attenuation information for the at least parts of the lines of response of the second subset. An image object of activity in the patient is reconstructed from the time-of-flight data including the lines of response of the first and second subsets. The reconstruction is a function of the first attenuation information along the lines of response of the first subset and the generated second attenuation information along the lines of response of the second subset. An image of the reconstructed image object is displayed.

In some embodiments, the attenuation information is CT data representing voxels of the CT volume. The time-of-flight data is obtained from different discrete, overlapping bed positions or during continuous bed motion. Alternatively, a longer scanner with only one bed position and not bed motion is used. Due to the limited extent of the CT volume, the time-of-flight data includes oblique lines of response where the lines of response of the second sub-set include the oblique lines of response extending beyond the CT volume. For reconstruction, the first and second attenuation information may be converted into attenuation coefficients along the first and second lines of response. The reconstruction is performed with the attenuation coefficients and/or attenuation correction factors derived therefrom. The first and second attenuation may be used in scatter modeling in the reconstruction. A PET image from the reconstruction is displayed.

In one embodiment, the second attenuation information is generated in response to input to the neural network of both a reconstruction from the time-of-flight data and the first attenuation information. The reconstruction being input may be from the time-of-flight data alone (e.g., Maximum Likelihood Automatic Activity reconstruction) or from the time-of-flight data and the first attenuation information. Other inputs may be alternatively or additionally used, such as a parameter defining a spatial extent of the CT volume relative to the lines of response of the second subset, attenuation correction factors, and/or sinogram data.

In another embodiment, the machine-learned neural network is configured based on training with training data including truncated attenuation maps as input samples and non-truncated attenuation maps as ground truth.

In a second aspect, a method is provided for reconstructing in positron emission tomography with partially known attenuation. A computed tomography (CT) scanner acquires the partially known attenuation for a CT volume of a patient. Attenuation outside of the CT volume is estimated with a machine-learned estimator. A PET image is generated based on the attenuation outside the CT volume and the partially known attenuation for the CT volume. The PET image is displayed.

In one embodiment, the machine-learned estimator estimates in response to input of the partially known attenuation for the CT volume and a reconstruction from detected emissions. In other embodiments, the machine-learned estimator estimates in response to input of spatial information of the CT volume relative to oblique lines of response from a positron emission tomography scan. The machine-learned estimator is a neural network or other machine-learned model. In a further embodiment, the PET image is generated by reconstructing with attenuation correction based on the partially known attenuation and the estimated attenuation.

In a third aspect, a system is provided for reconstructing in PET with partially known attenuation. An x-ray scanner is configured to obtain attenuation data for a patient volume. A bed is configured to move to scan different parts of a patient in a positron emission tomography (PET) scan. Rings of detectors spaced axially are operable to perform the PET scan along lines of response between the detectors. A first set of lines of response oblique to the axial spacing of the detectors extend out of the patient volume. A processor connected to the detectors is configured to reconstruct activity distribution using time-of-flight for detected emissions along the lines of response including the first set and others. The activity distribution includes corrections for the first set of lines of response extending out of the patient volume. The corrections are based on output of a neural network. A display is configured to display a PET image of the activity distribution.

In a further embodiment, the neural network is configured to output attenuation beyond the patient volume. The processor is configured to reconstruct from the detected emissions of the PET scan with attenuation correction from the attenuation data for the patient volume and the attenuation beyond the patient volume. Various inputs to the neural network may be used, such as the neural network being configured to output in response to input of the attenuation data for the patient volume and a reconstruction of the detected emissions. The processor is configured to reconstruct the activity distribution from the detected emissions, the attenuation data for the patient volume, and the output of the neural network. In another embodiment, the neural network is configured to output attenuation corrections for the first set of the lines of response.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A more uniform sensitivity emission image is reconstructed with partially known axial attenuation information in a PET-CT scanner. In PET-CT, the axial length of image reconstruction is defined by the CT scan, which delivers an axial extent-dependent radiation dose. The beginning and end scanning points for CT and therefore PET scans are typically chosen in such a way that the PET scan is performed with a particular number of beds or range of bed movement. Still, the edge planes will have lower sensitivity due to the absence of oblique LOR attenuation factors unless the CT volume and corresponding x-ray dose extends beyond the region of interest.

An artificial intelligence provides prior information for the reconstruction. This prior information corrects for the missing attenuation. For example, the artificial intelligence estimates the missing attenuation based on the learned knowledge base, allowing for scaling of attenuation correction factors and/or enhancement of scatter estimation in PET reconstruction. In other examples, the artificial intelligence estimates the attenuation correction factors (ACFs) or corrections to the reconstructed PET image object to correct for the missing attenuation information. In any of these approaches, the PET image has improved quality due to or emulating greater sensitivity uniformity and/or scatter estimation provided by the artificial intelligence for outside the CT volume.

ACFs and emission activity may be defined only up to a scaling parameter. This is due to the fact that ACFs and emission activity projections are multiplied in the modeling of measured data. This scaling issue may be avoided by enforcing constraints on the attenuation coefficients in TX-less algorithms that reconstruct the attenuation map. Since the attenuation map is not reconstructed, but rather the ACFs are used directly, this approach of avoidance is not used. Instead, the scaling parameter is defined implicitly by the interconnection between the direct and oblique LORs, for which the ACFs are known from the CT, and those edge oblique LORs for which the ACFs is estimated by the artificial intelligence. Partial ACF knowledge restores attenuation information for the uniform sensitivity of PET reconstructed volume edge planes.

Figure 1:
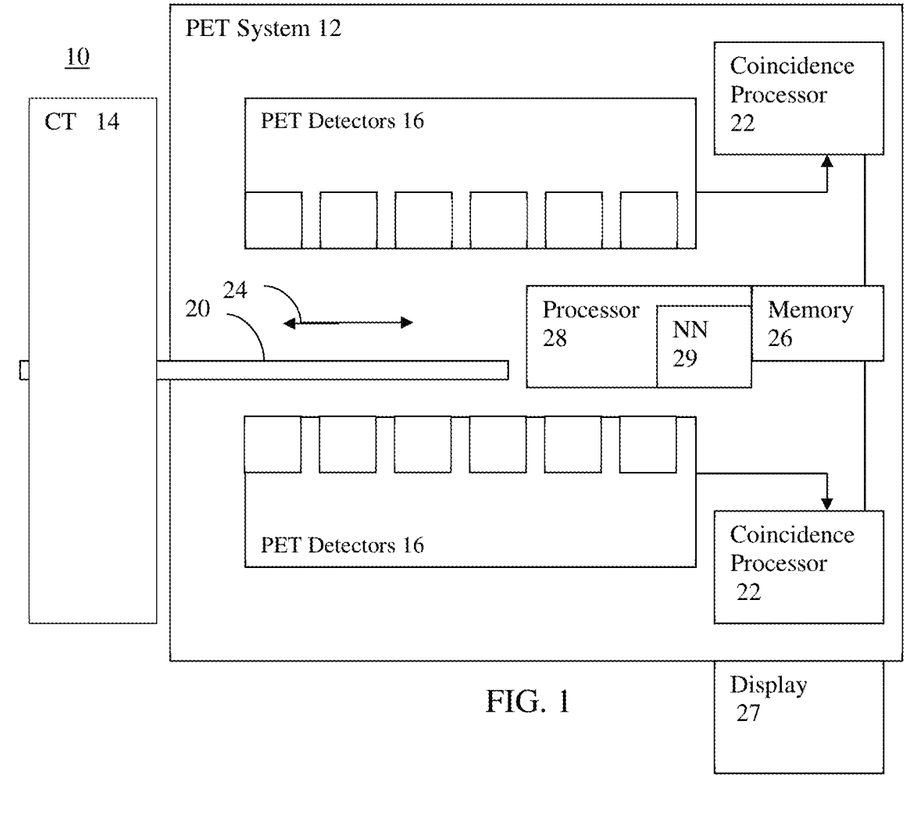
FIG. 1 is a block diagram of a system, according to one embodiment, for reconstructing in positron emission tomography with partially known attenuation.

FIG. 1 shows a PET-CT system 10 for reconstructing in positron emission tomography (PET) with partially known attenuation. The neural network 29 or other artificial intelligence corrects for missing attenuation information. The correction may be by directly estimating the missing attenuation, estimating missing or incomplete attenuation correction factors for oblique lines of response, or by correcting intensity of activity in a reconstructed object. The PET-CT system 10 performs the method of FIG. 4 or another method to reconstruct and PET image with partially known attenuation while correcting for the missing attenuation.

The PET-CT system 10 includes a CT scanner 14 and PET system 12. The PET system 12 includes rings of detectors 16, a bed 20, coincidence processors 22, a memory 26, a display 27, and a processor 28. The processor 28, memory 26, and/or display 27 are part of the PET system 12 or are separate (e.g., a computer or workstation). Additional, different, or fewer components may be provided. For example, the system is a computer without the detectors 16 and bed 20, instead relying on data acquired by a separate scanner. As another example, the PET-CT system 10 includes power supplies, communications systems, and user interface systems.

The CT system 14 includes an x-ray source and opposing detector mounted in a gantry. The CT system 14 is an x-ray scanner configured to obtain attenuation data for a patient volume. The gantry moves the source and detector about the patient for scanning. The processor 28 or a different processor computes the attenuation of the x-rays at different voxels within the scan volume. Any now known or later developed CT system may be used. Other x-ray scanners, such as a CT-like C-arm scanner, may be used.

The CT system 14 is within a same housing as the PET system 12 or is spaced apart by and connected by a common track for the bed 20. Completely separate CT system 14 and PET system 12 may be used.

The bed 20 is a gurney, table, or other support to hold an examination subject, such as a patient. A robot, gears, cable, track, and/or other device move the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems, such as a cylindrical or polar coordinate system, may be used.

In one embodiment, the movement is continuous, at least during part of the scanning. The bed 20, while supporting the patient, is moved at a same or a varying velocity along the axial dimension 24. For example, the head of the patient is scanned with 1.5 mm/s movement of the patient, and the torso is scanned with 1.0 mm/s movement of the patient. Other combinations of the same or different rates, with or without a greater number of different velocities, may be used. The movement may pass the patient through the bore or merely partly into the bore. The movement is with or without acceleration. In one embodiment, the movement is back and forth, scanning the patient multiple times in a cyclical pattern. A single pass may be used in other embodiments.

In other embodiments, the bed 20 is positioned to two or more discrete bed positions. PET scanning occurs over a period with the stationary bed at each bed position. The bed positions are spaced so that the PET scan volume (e.g., the volume within or between the detectors 16) overlaps in the adjacent bed positions. The bed 20 is moved from position to position in order to acquire PET data for the PET scan.

In yet another embodiment, the bed 20 is stationary. The detectors 16 may be long, such as 1 meter, allowing a scan of the torso of the patient without movement of the bed continuously or to different positions. Only one bed is acquired.

With either stationary bed positions or continuous bed motion, the bed 20 moves the patient to scan the CT volume for emissions as part of the PET scan. For more uniform sensitivity, the end extent of the bed positions extends the detectors 16 to collect emissions along oblique lines of response through the edge or end of the CT volume. CT information is not available along the entire length of the oblique lines of response extending past the CT volume. Only partial attenuation information is available due to the spatial limit of the CT volume. Attenuations beyond the CT volume are not provided despite some of the oblique lines of response in the PET scan extending beyond the CT volume. For one bed position (i.e., no bed motion), the CT volume may be less than the extent of the measurements of emissions for this one bed position. For example, the CT volume is less than 1 meter long (e.g., 0.5 or 0.75 meters) in order to reduce radiation exposure where the detectors 16 measure over a 1 meter range.

The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used. Solid-state or semiconductor detectors may be used.

Figure 2:
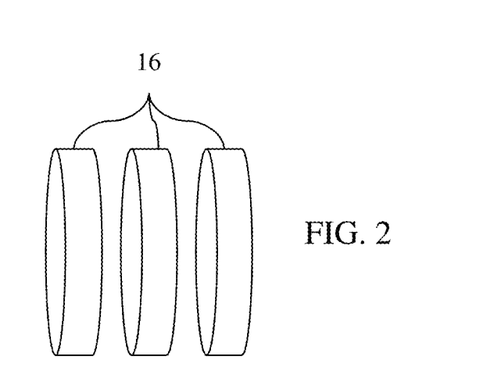
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart but are placed adjacent or abutting each other. Any gap may be provided between blocks within a ring, detectors within a block, and/or between rings. Any number of detectors in a block (e.g., 8 or 16), detector blocks in a ring, and/or rings may be used. The rings may extend completely or only partially around the bore.

The PET system 10 is a nuclear imaging system. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays. The timing, as prompt data, may also indicate the time-of-flight, providing information generally about where along a line of response the emission occurred.

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22 as well as general position along the line of response of the emission. Pairs of gamma rays associated with a same positron emission are determined. Based on the detected event, a line-of-response is determined given the detectors involved in the detection of that event.

As the bed 20 moves, the patient passes through the rings. A given part (e.g., organ) of the patient is within different rings at different times due to the continuous bed motion or bed position. The line-of-responses for the same part of the patient and corresponding actual three-dimensional location (i.e., point along the line-of-response) is at different locations at different times. The detectors 16 continue to detect gamma rays as the bed 20 and patient moves so different lines-of-response may be for the same part of the patient at different positions within the bore. For scanning with one bed position, the detectors 16 detect gamma rays for that one bed position.

The lines of response include direct plane LORs corresponding to lines perpendicular to the axis of movement of the bed 20 or axial spacing of the detectors 16. The lines of response also include oblique LORs corresponding to lines that are at a non-perpendicular angle to the axis of movement of the bed 20 but still intersecting the detectors 16. At least some of the oblique lines of response extend beyond the CT volume, such as oblique lines of response at the bed positions at the ends of the PET scan. Where the bed 20 moves to provide PET scanning beyond the CT volume, direct lines of response may be outside of the CT volume so may be missing attenuation information.

The detected events are passed to the memory 26 and/or processor 28. The processor 28 connects with the detectors 16, such as through the coincidence processors 22. The processor 28 also connects with the CT system 14 to receive attenuation information.

The processor 28 is a general processor, digital signal processor, graphics processing unit, application specific integrated circuit, artificial intelligence processor, field programmable gate array, digital circuit, analog circuit, combinations thereof, or other now known or later developed device for processing detected line-of-response events, correcting for missing attenuation, and/or reconstructing. The processor 28 is a single device, a plurality of devices, or a network. For more than one device, parallel or sequential division of processing may be used. Different devices making up the processor 20 may perform different functions, such as one processor for handling line of response emission information and attenuation information (e.g., implementing the artificial intelligence) and another processor for reconstructing the object (i.e., patient) space. In one embodiment, the processor 28 is a control processor or other processor of the PET-CT system 10 or the PET system 12. In other embodiments, the processor 28 is part of a separate workstation or computer.

The processor 28 operates pursuant to stored instructions to perform various acts described herein. The processor 28 is configured by software, firmware, and/or hardware to perform any or all of the acts of FIG. 4. The operation and configuration of the processor 28 is first described in general below. An example implementation is described in more detail in the following discussion of FIG. 4.

The processor 28 is configured to reconstruct the activity distribution using the time-of-flight (TOF) for detected emissions along the lines of response. The TOF from the direct plane and oblique lines are used to reconstruct the activity distribution. To account for differences in attenuation due to different tissues or obstructions along the different lines of response, the ACFs or integrated attenuations along the corresponding lines of response are used in the reconstruction. For some of the lines of response, attenuation information may not be available. Where part of the line of response through the patient includes voxels or regions for which attenuation information is not available (i.e., extends beyond the CT volume), part of the contributing attenuation for the ACF is not provided. As a result, all the attenuation and complete ACF is not known for that line of response. Similarly, the reconstruction may account for scattering using attenuation. Due to the limited extent of the CT volume, scattering from beyond the volume may not be accounted for in the reconstruction.

Figure 3:
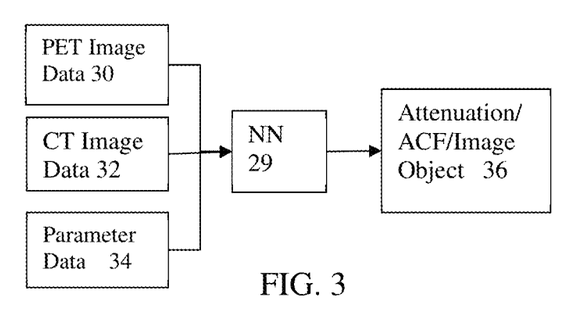
FIG. 3 shows example inputs and outputs for an example neural network used to account for missing attenuation information.
Figure 4:
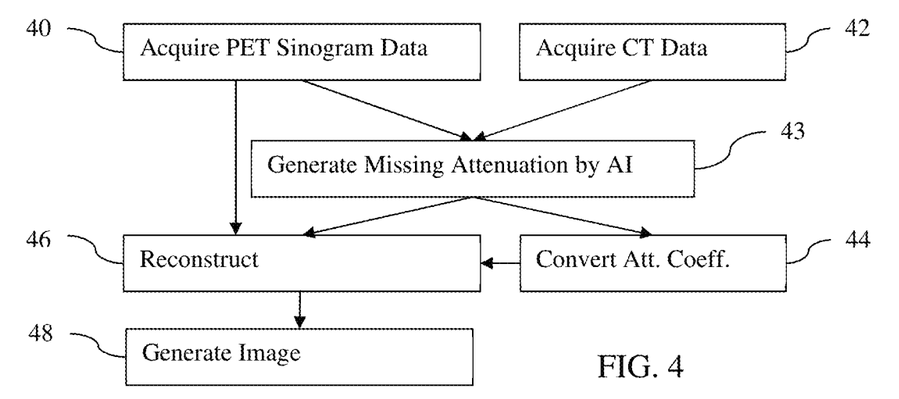
FIG. 4 is a flow chart of an embodiment of a method for reconstructing in positron emission tomography with partially known attenuation.

The processor 28 is configured to reconstruct the activity distribution including corrections for both the lines of response for which attenuation is available and for lines of response for which the CT volume does not include at least some attenuation (i.e., lines of response that extend out of the CT volume). The reconstruction may alternatively or additionally account for scattering based on attenuation beyond the CT volume. To correct for the missing attenuation, an artificial intelligence (e.g., a neural network 29) outputs information used in the correction. Any neural network may be used, such as a U-Net with three convolutional layers at each level of two levels and a bottleneck where skip connections are provided for each level. FIG. 3 shows example outputs and inputs. In one embodiment, the neural network 29 is configured to output attenuations 36 beyond the patient volume. The attenuations from the CT volume and the output attenuations 36 from the neural network 29 are used for attenuation correction and/or scatter estimation in PET reconstruction. FIG. 4 shows an example method implementing this embodiment. In another embodiment, the neural network 29 is configured to output attenuation correction factors 36 for the lines of response extending out of or not in the CT volume. The output attenuation correction factors 36 and attenuation correction factors from the CT volume are used in PET reconstruction. In yet another embodiment, the neural network 29 corrects for the missing attenuation information by altering the reconstructed PET image object 36. The intensities (i.e., level of activity) of some voxels are altered to emulate the intensities where full attenuation information is available.

The artificial intelligence outputs the corrections in response to input information. FIG. 3 shows input of PET image data 30 (e.g., reconstructed object), CT image data 32 (e.g., attenuations or attenuation correction factors), and/or spatial parameters 34 indicating the locations of lines of response with missing attenuation information. The PET and/or CT image data may instead be data prior to reconstruction, such as sinogram and/or projections. The inputs 30, 32, 34 are provided to the neural network 29 to generate the output. For example, the output is generated in response to input of (a) the attenuation data for the patient volume (e.g., CT data 32 of the CT volume) and a reconstruction of the detected emissions. The reconstruction of the detected emissions may be from the detected emissions without attenuation or from the detected emissions and the attenuation from the CT volume (i.e., from the partial attenuation information available). In another example, the output is generated in response to the CT data 32 without any PET data 30 or vice versa. In yet another example, the output is in response to input of spatial information, such as any representation that may indicate the locations for which attenuation is missing (e.g., parameter data 34). Any combination of different types of data may be input.

In one embodiment, the processor 28 is configured to reconstruct from the detected emissions of the PET scan with attenuation correction from the attenuation data for the CT volume and the estimated attenuation beyond the CT volume. For example, the processor is configured to reconstruct the activity distribution from the detected emissions, the attenuation data (e.g., CT data) for the CT volume, and the output of the neural network. The reconstruction may use ACFs as the attenuation data.

The processor 28 uses the events (e.g., line-of-response events or PET data 30), attenuation or CT data 32, parameter data 34, attenuation correction factors, and/or other information stored in the memory 26 for processing. For processing, the data bypasses the memory 26, is temporarily stored in the memory 26, or is loaded from the memory 26.

The detected events, line-of-response information (e.g., sinograms), time step, prompt data, attenuation information, ACF, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 12 or a remote workstation or database, such as a PACS memory.

The memory 26 is additionally or alternatively a non-transitory computer readable storage medium with processing instructions. The memory 26 stores data representing instructions executable by the programmed processor 28 for reconstructing in positron emission tomography (PET) with partially known attenuation. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 12 may include the display 27. For example, the processor 28 reconstructs the patient or object being scanned from the line-of-response PET data and the attenuation data. The reconstruction, reconstructed object, or reconstructed activity distribution is used for three-dimensional rendering, multi-planar reconstruction, or two-dimensional imaging of the function of the object or patient. The images are displayed on the display 27. The display 27 is a CRT, LCD, plasma screen, projector, printer, or other output device for showing a PET image of the activity distribution. The PET image may be a qualitative or quantitative image.

FIG. 4 shows one embodiment of a method for reconstructing in PET with partially known attenuation. The neural network 29 or other artificial intelligence is used to correct for missing attenuation in PET imaging. In the embodiment of FIG. 4, the correction is by estimation of the missing attenuation. In other embodiments, the correction is by estimation of incomplete ACFs or by alteration or replacement of reconstructed activity.

The method of FIG. 4 is implemented by the processor 28, the PET system 12, the PET-CT system 10, and/or other component or system. Additional, different, or fewer acts may be performed. For example, act 48 is not performed. The acts are performed in the order shown or a different order. Acts 40 and 42 may be performed in any order or simultaneously. As another example, act 46 may be performed prior to act 43 for input of a reconstructed activity for artificially intelligence-based generation of the missing attenuation and performed again using the generated attenuation information to reconstruct for imaging.

In act 42, attenuation information is acquired. A CT scan of the patient is performed by the CT scanner. Other x-ray scanners to measure the attenuation at different locations or along lines through the patient may be used. Alternatively, the attenuation information is acquired from memory, such as attenuation information from a previously performed CT scan.

The CT scan is of a volume of the patient. Any range of the patient may be scanned, such as from the hips to the neck. The entire patient may be scanned. The CT scan provides measures of attenuation of the x-ray energy at different locations, such as voxels, within the patient. The attenuation of the voxels is computed by tomography from a sequence of x-ray scans from different angles through the patient. The resulting CT intensity data represents voxels of the CT scan volume. The CT intensity data is the known attenuation data. Attenuation for locations in the CT scan volume is known (i.e., partially known attenuation) yet attenuation for locations beyond or outside of the axial extent of the CT scan volume is not known.

In act 40, PET sinogram data is acquired. Time-of-flight (TOF) data for emissions detected along a plurality of lines of response is acquired. The acquisition is by scanning with the PET scanner with a plurality of detectors. In alternative embodiments, the acquisition is by transfer or upload from a memory.

Figure 5:
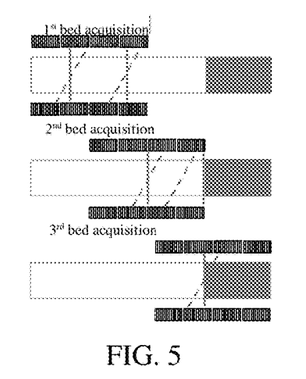
FIG. 5 illustrates example bed positions and lines of response.
Figure 7:
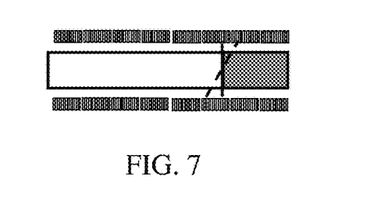
FIG. 7 illustrates a single bed position and lines of response.

Gamma rays are detected by one or more rings of detectors or other grouping of detectors. The patient ingests or is injected with a radiopharmaceutical. The radiopharmaceutical includes an isotope. The isotope decays over time, resulting in generation of a positron.

Where each ring is formed from a block of X detectors along the axial direction, X planes are defined. For example, each block includes 16 detectors, so 16 planes are provided for each block. Where there are 50 rings, 530 planes are defined. FIG. 5 shows example lines of response for three different bed positions as solid vertical lines. These lines of response are direct plane lines. For each bed position, emissions along 530 or other number of direct plane lines of response may be detected. FIG. 7 shows an example line of response for an end direct plane where a single bed position Since the detectors have an axial extent, emissions from lines of response oblique to the axis of the bed or detectors are detected. Example oblique lines of response are shown in FIGS. 5 and 7 as dashed lines.

In both continuous bed motion and use of discrete bed positions, the same detectors are used to detect positron-electron annihilations from different parts of the patient. Due to the motion or change in position, annihilations in a same part of the patient may be detected at different rings at different times even where the line of gamma ray propagation is the same relative to the patient for each time. Of course, the line of propagation may be different at different times for a same location of the patient.

Line-of-response events from a patient are detected. The acquisition occurs over any period. For example, the acquisition is over 1, 10, 100, or other number of minutes. The PET scanning acquires detected emission events for functional information. The detected gamma rays are checked for coincidence to define lines-of-response, and the time difference or relative timing for coincident detections is recorded as prompt data. Any time window may be used for coincidence processing, such as 0.2 microsecond coincidence time window. Each detected emission event corresponds to a line or part of a line through a patient. By detecting emission events from different angles around a patient, a volume may be reconstructed.

In one embodiment, the time-of-flight data is obtained from different discrete, overlapping bed positions. Scanning is performed for each of any number of different overlapping bed positions. FIG. 5 shows an example with three different bed positions. In alternative embodiments, a single bed position is provided, such as shown in FIG. 7. In another embodiment, the time-of-flight data is obtained while the bed is moving the patient. The movement is over any range of motion, such as for scanning all or only a part of the patient. The bed may move cyclically during the period, such as moving back and forth once, five times, ten times, twenty times, forty times, or other number of times. Alternatively, the bed moves in one direction only during the scan.

The motion of the bed is continuous over at least a portion of the acquisition period. Continuous is used in the sense of motion occurring during the scanning. The continuous motion may cease or have different velocities for a part of the scanning. With cyclical motion, there may be one or more times of no motion and parts of the period with acceleration or deceleration. In alternative embodiments, a constant velocity is provided.

Figure 6A:
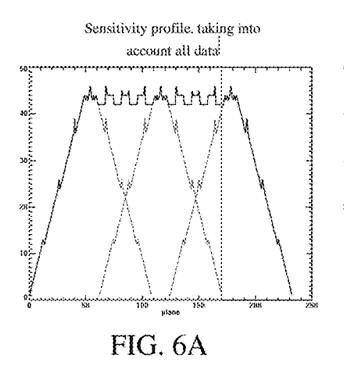
FIGS. 6A and 6B are example sensitivity profiles for the bed positions of FIG. 5.
Figure 6B:
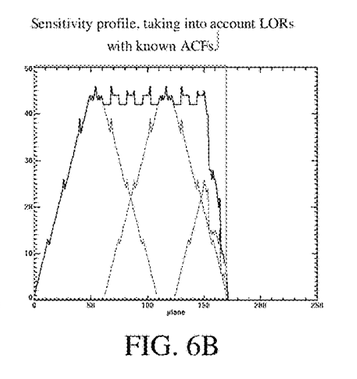

The acquisition is for any part of the patient. For the edge (e.g., beginning and ending) axial positions of the bed, the resulting reconstruction may have less sensitivity. The edge axial planes of the reconstructed volume suffer from a lower sensitivity than the central axial planes because the edges are reconstructed from a smaller set of oblique LORs. The CT scan defines the axial extent of the reconstructed volume (see white box of FIGS. 5 and 7). Typically, the axial coverage length is chosen in such a way that a certain number of overlapping PET bed positions completely sample the reconstruction volume, as defined by the CT volume. A single bed position may completely sample the reconstruction volume. The bed overlap is designed to achieve a uniform sensitivity by summing the roughly triangular axial sensitivity profiles corresponding to each bed position (see FIG. 6A). Nevertheless, the edge planes of the last or only bed acquisition still have a lower sensitivity because only direct plane LORs are available. This problem can be solved by acquiring an additional bed position (e.g., the 3rd bed position shown in FIG. 5) or moving the bed over a greater range in continuous bed motion, so as to make the axial sensitivity uniform throughout the CT defined volume. As represented by the dashed lines in FIG. 4, the attenuation correction factors (ACFs) for some oblique LORs are not available from the CT scan because these LORs pass outside the CT defined volume (white box). As a result, the edge axial planes may still suffer from a lower sensitivity if only LORs with CT-known ACFs are used during reconstruction, as shown in FIG. 6B. The sensitivity profiles of FIGS. 6A and 6B are obtained by Inverse Single Slice Rebinning (ISSRB) assuming axially uniform objects.

The attenuation information is available for some lines of response and not for at least some other lines of response. For example, oblique lines of response by the edges of the CT volume include portions along the line without attenuation information.

In act 43, the processor estimates attenuation outside of the CT volume. A machine-learned estimator estimates the missing attenuation. Alternatively, the estimator estimates missing or corrected ACFs for lines of response that, at least in part, extend beyond the CT volume. In another alternative, the machine-learned estimator estimates intensity change or activity level to correct for the reconstructed activity distribution resulting from missing attenuation information.

Machine learning uses training data of many hundreds or thousands of samples of inputs with labeled ground truth output or outputs for each sample. The training data is used as knowledge of past cases to train the classifier to generate the output for unseen cases. The training associates the features of the input vector with output corrections (i.e., an adjustment, missing data, and/or corrected data).

Any machine learning or training and resulting estimator may be used. A probabilistic boosting tree, support vector machine, neural network, sparse auto-encoding classifier, Bayesian network, regression model, or other now known or later developed machine learning may be used. Any semi-supervised, supervised, or unsupervised learning may be used. Hierarchal or other approaches may be used. In one embodiment, the estimator is a neural network trained with deep learning. As part of learning features that distinguish between different outputs, the estimator is also machine trained to output based on the learned features.

In one embodiment, the deep learning is to train a machine-learned model to estimate missing attenuations. For example, each sample input vector includes CT data (e.g., measured attenuations for the patient volume), PET data (e.g., reconstructed activity with or without reconstruction using the known attenuations), and/or parameter data (e.g., indication of locations of missing attenuation, such as planes for which attenuation is to be estimated). The ground truth provided for each sample in the training data includes the missing attenuation or the known attenuation in combination with the missing attenuation. The ground truth may be other outputs, such as ACFs or correction in the reconstructed object.

Any deep learning approach or architecture may be used. For example, a convolutional neural network is used. The network may include convolutional, sub-sampling (e.g., max pooling), fully connected layers, softmax, and/or other types of layers. By using convolution, the number of possible features to be tested is limited. The fully connected layers operate to fully connect the features as limited by the convolution layer after maximum pooling. Other features may be added to the fully connected layers, such as the parameter data defining the spatial extent of the lines of response and the CT volume. Any combination of layers may be provided. Hierarchical structures are employed, either for learning features or representation or for estimation or regression.

In one embodiment, a generative network is used, such as an image-to-image network, a U-Net generator, or a generative adversarial network (GAN of a generator and a discriminator). Due to input of spatial distribution (e.g., CT data and PET data as a reconstruction) and output of spatial distribution (e.g., missing attenuation by location), an image-to-image network (e.g., U-Net) may be used. Alternatively, the estimator sequentially estimates the attenuation location-by-location based on the input vector.

In training, truncated attenuation maps (i.e., CT volume that does not cover all of the locations along the lines of response) are used as sample inputs. Other data, such as PET data, may be included in the sample inputs. Non-truncated attenuation maps (i.e., CT volume covering all the locations) are used as ground truth. Other ground truths, such as ACFs or image object corrections, may be used as ground truth. The machine training with the training data configures the machine-learned neural network or estimator to output estimates given previously unseen inputs.

The machine-learned model, trained with or without deep learning, is trained to output in response to the input vector. The machine learning uses training data with ground truth to learn to estimate based on the input vector. The resulting machine-learned model defines how to extract values for features from the input and/or other features and output the corrections.

The input feature vector includes personalized or patient-specific information, including the CT data and/or the PET data measured for the patient. The machine-learned model outputs any correction, such as missing attenuations, specific to the patient. Due to the personalized input, the estimated output may more likely reflect the attenuation in the patient.

In act 43, the machine-learned estimator (e.g., neural network) generates attenuation information for the parts of the lines of response not located in the CT volume. For example, the oblique lines of response on the edge planes or near the edge planes include at least part of the lines outside the CT volume. The estimator estimates the attenuation for the locations outside the CT volume.

The machine-learned estimator generates the output in response to input for the patient. For example, (a) a reconstruction from the time-of-flight data with or without the attenuations for the CT volume and (b) the attenuations for the CT volume are input. The PET data (e.g., the reconstruction) is subject to attenuation outside the CT volume, so may indicate the attenuation. The CT volume may indicate attenuation likely beyond the volume, such as due to commonality in variance of anatomy in the population. The reconstruction from the time-of-flight data and the known attenuation information for a given patient is input. The partially known attenuation information, a reconstruction from detected emissions, and/or spatial information of the CT volume relative to oblique lines of response from a positron emission tomography scan are input to and used by the estimator to correct for missing attenuation.

The attenuation information is converted into attenuation coefficients in act 43. The attenuation information is converted to account for differences in energy level between the x-rays and the photons of positron emission. For example, the attenuation information is converted into 511 coefficients.

The conversion also accounts for the lines of response. The measured attenuation information is for voxels in the CT volume. Any given line of response traverses the volume, so the attenuation along the line is an integral of the attenuations of the line. For the planar and oblique lines of response with known attenuation, at least through the patient, the attenuation information is converted into attenuation coefficient factors (ACFs). Known ACF is provided for only a subset of all of the lines of response. Some of the oblique lines of response have known attenuation through the patient.

Other oblique or direct lines of response have at least a part of the line with unknown attenuation in the patient. The lines of response passing outside of the CT volume while within the patient have missing attenuation information. The ACF for such a line is incomplete, so unknown. In the example of FIG. 4, the example oblique lines of response at the end bed positions or ends of the only bed position that pass partly out of the CT volume have missing attenuation information. While some attenuation is known, the attenuation along the entire line within the patient is not known. Accordingly, the ACF is not known.

Since the missing attenuation is generated in act 43, the ACFs for the lines of response extending out of the CT volume may be determined. The measured attenuations of the CT volume and the machine-learned estimator estimates of attenuation outside the CT volume are converted to ACFs for all or most of the lines of response. Both sources of attenuation may be used for the ACF of a given line of response.

The processor generates a PET image based on the attenuation outside the CT volume and the partially known attenuation for the CT volume. For example, the ACFs from act 44 are used to correct for attenuation in the reconstruction of act 46. The reconstructing of act 46 uses the attenuation correction based on both the partially known attenuation and the estimated attenuation. As another example, the attenuations from acts 42 and 43 are used for scatter estimation in the reconstruction of act 46. In other embodiments, the processor generates the PET image by reconstruction with the partial attenuations and correction of intensities or activity level of the reconstructed object or pixels in the rendered image based on output corrections by the neural network. In yet other embodiments, the reconstruction uses ACFs generated in act 43 to generate the PET image.

Acts 46 and 48 are performed after acts 43 and/or 44 for the embodiments generating incomplete ACFs or missing attenuations in act 43. In act 46, an image object of the patient is reconstructed from the time-of-flight data for the lines of response within and the lines of response at least partially extending beyond the CT volume. The object space is reconstructed form the PET TOF, such as from prompt or sinogram data. The activity distribution in three-dimensions is reconstructed. The activity distribution is used for imaging, such as volume rendering, multi-planar reconstruction, or planar imaging.

Any reconstruction may be used. In one embodiment, the reconstruction is a Poisson iterative reconstruction, such as a maximum likelihood reconstruction. OSEM, FORE, or other reconstructions may be used. The reconstruction estimates the object or patient space from the lines-of-response. The detected events are used to iteratively determine the object space using forward, backward, or forward and backward projection.

In one approach, an initial reconstruction is performed using the partial attenuation information or not using any attenuation information (e.g., Maximum-Likelihood Automatic Activity). This initial reconstruction is used as an input to the neural network in act 43. The initial reconstruction may use the approach described in U.S. Pat. No. 9,155,514, where the objective function for the reconstruction makes use of the known ACF and a model of the ACF derived from the emission information, such as the prompt data, for the unknown ACF. The TOF data itself includes attenuation information, so may be used to create the model for the missing ACFs. In one embodiment, the model is a Gaussian smoothed function of the time-of-flight data for the lines of response with missing attenuation information. During iterative reconstruction, the activity image or distribution of a previous iteration of the reconstruction is used to model the ACF for lines of response with missing ACF. The emission data is projected along the lines of response with missing ACF. The model may use normalized, smoothed prompt data, which is pre-corrected for background.

Once the ACFs and/or attenuation for the CT volume and the locations beyond the CT volume are generated, the reconstruction of act 46 is performed using the PET TOF data, the ACFs for all the lines of response (ACF for attenuation along each entire line), and/or the attenuation for all the lines of response (attenuation along each entire line).

The reconstruction is a function of the attenuation information along the lines of response of the lines entirely within the CT volume and the attenuation information along the lines of response that extend beyond the CT volume. The generated attenuation information provides more accurate ACFs for oblique lines of response near the edges of the CT volume. The reconstruction accounts for the attenuation using ACFs for the lines of response. The lines of response used include lines of response for which ACF is known and lines of response for which ACF is not known. The PET emission distribution is reconstructed from emission data for lines of response and from attenuation coefficients for some but not all of the lines of response.

In act 48, an image is displayed. The reconstructed activity or emission distribution as an image object is used to create a PET image. An image is generated by reconstructing the object space and then rendering or imaging from the reconstructed object. The image is of the patient, such as a PET image showing function or uptake of the radiopharmaceutical. The image benefits from machine-learned estimation of corrections for missing attenuation. More accurate imaging less sensitive to noise and truncation is provide.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for reconstructing in positron emission tomography with partially known attenuation, the method comprising:
acquiring, with a computed tomography (CT) scanner, first attenuation information for a CT volume of a patient, the first attenuation information comprising the partially known attenuation;
acquiring, with a positron emission tomography (PET) scanner having a plurality of detectors, time-of-flight data along lines-of-response from emissions, the first attenuation information available for a first subset of the lines-of-response and unavailable for at least parts of the lines of response of a second subset of the lines-of-response;
generating, by a machine-trained neural network, second attenuation information for the at least parts of the lines of response of the second subset;
reconstructing an image object of activity in the patient from the time-of-flight data including the lines of response of the first and second subsets, the reconstructing being a function of the first attenuation information along the lines of response of the first subset and the generated second attenuation information along the lines of response of the second subset; and
displaying an image of the reconstructed image object.

2. The method of claim 1 wherein acquiring the attenuation information comprises acquiring CT data representing voxels of the CT volume.

3. The method of claim 1 wherein acquiring the time-of-flight data comprises obtaining the time-of-flight data from a single bed position.

4. The method of claim 1 wherein acquiring the time-of-flight data comprises obtaining the time-of-flight data during continuous bed motion.

5. The method of claim 1 wherein acquiring the time-of-flight data comprises acquiring the time-of-flight data for oblique ones of the lines of response, the lines of response of the second sub-set being the oblique lines of response extending beyond the CT volume.

6. The method of claim 1 further comprising converting the first and second attenuation information into attenuation coefficients along the first and second lines of response, and wherein reconstructing comprises reconstructing with the attenuation coefficients.

7. The method of claim 1 wherein generating comprises generating in response to input of a reconstruction from the time-of-flight data and the first attenuation information to the neural network.

8. The method of claim 7 wherein generating comprises generating in response to the input of the reconstruction, the reconstruction from the time-of-flight data and the first attenuation information.

9. The method of claim 1 wherein generating comprises generating in response to input of a parameter defining a spatial extent of the CT volume relative to the lines of response of the second subset.

10. The method of claim 1 wherein generating comprises generating with the machine-learned neural network configured based on training with training data including truncated attenuation maps as input samples and non-truncated attenuation maps as ground truth.

11. The method of claim 1 wherein displaying the image comprises displaying a PET image.

12. A method for reconstructing in positron emission tomography with partially known attenuation, the method comprising:
acquiring, with a computed tomography (CT) scanner, the partially known attenuation for a CT volume of a patient;
estimating attenuation outside of the CT volume with a machine-learned estimator;
generating a positron emission tomography image based on the attenuation outside the CT volume and the partially known attenuation for the CT volume; and
displaying the positron emission tomography image.

13. The method of claim 12 wherein estimating the attenuation comprises estimating by the machine-learned estimator in response to input of the partially known attenuation for the CT volume and a reconstruction from detected emissions.

14. The method of claim 12 wherein estimating comprises estimating with the machine-learned estimator comprising a neural network.

15. The method of claim 12 wherein estimating comprises estimating in response to input of spatial information of the CT volume relative to oblique lines of response from a positron emission tomography scan.

16. The method of claim 12 wherein generating comprises reconstructing with attenuation correction based on the partially known attenuation and the estimated attenuation.

17. A system for reconstructing in positron emission tomography (PET) with partially known attenuation, the system comprising:
- an x-ray scanner configured to obtain attenuation data for a patient volume;
- a bed configured to move to scan different parts of a patient in a positron emission tomography (PET) scan;
- rings of detectors spaced axially operable to perform the PET scan along lines of response between the detectors, a first set of lines of response oblique to the axial spacing of the detectors extending out of the patient volume; and
- a processor connected to the detectors, the processor configured to reconstruct activity distribution using time-of-flight for detected emissions along the lines of response including the first set and others, the activity distribution including corrections for the first set of lines of response where extending out of the patient volume, the corrections being based on output of a neural network when input at least the attenuation data; and
- a display configured to display a PET image of the activity distribution.

18. The system of claim 17 wherein the neural network is configured to output attenuation beyond the patient volume, and wherein the processor is configured to reconstruct from the detected emissions of the PET scan with attenuation correction from the attenuation data for the patient volume and the attenuation beyond the patient volume.

19. The system of claim 17 wherein the neural network is configured to output in response to input of the attenuation data for the patient volume and a reconstruction of the detected emissions, and wherein the processor is configured to reconstruct the activity distribution from the detected emissions, the attenuation data for the patient volume, and the output of the neural network.

20. The system of claim 17 wherein the neural network is configured to output attenuation corrections for the first set of the lines of response.

* * * * *